United States Patent [19]
Jaquez et al.

[11] Patent Number: 5,893,827
[45] Date of Patent: Apr. 13, 1999

[54] DEVICE FOR OBVIATING ERECTILE DYSFUNCTIONING

[76] Inventors: Ramon E. Jaquez, 35-06 103rd St. Apt. 2, Corona, N.Y. 11368; Pedro Garcia, 251-15 Horace Harding Blvd., Little Neck, N.Y. 11363

[21] Appl. No.: 09/105,386
[22] Filed: Jun. 26, 1998
[51] Int. Cl.⁶ .................................................. A61F 5/41
[52] U.S. Cl. .................................................. 600/38
[58] Field of Search .................................. 600/38–41

[56] References Cited

U.S. PATENT DOCUMENTS

| | | |
|---|---|---|
| 4,660,551 | 4/1987 | Nishimura ............................ 600/41 |
| 4,989,592 | 2/1991 | Chang ................................. 600/38 |
| 5,244,454 | 9/1993 | Coates ................................ 600/41 |
| 5,728,043 | 3/1998 | Yong ................................... 600/39 |

*Primary Examiner*—Samuel Gilbert
*Attorney, Agent, or Firm*—Myron Amer PC

[57] ABSTRACT

In contrast to exiting flow-restricting penis encircling rings applying a single selected pressure as determined by their size and construction material, there is provided a pressure-applying device to counter venous leakage having an operating mode of making available a range of pressures so that a user can select a pressure from the range, prior use of the device, as might be determined from trial and error that is most effective for his artery system, all to the end of maintaining an erectile penis condition.

1 Claim, 3 Drawing Sheets

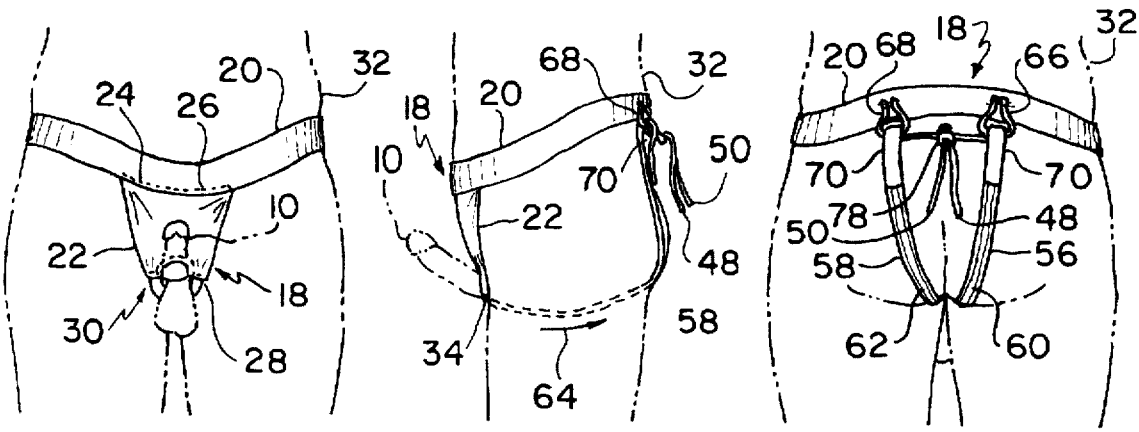
FIG.1  FIG.2  FIG.3
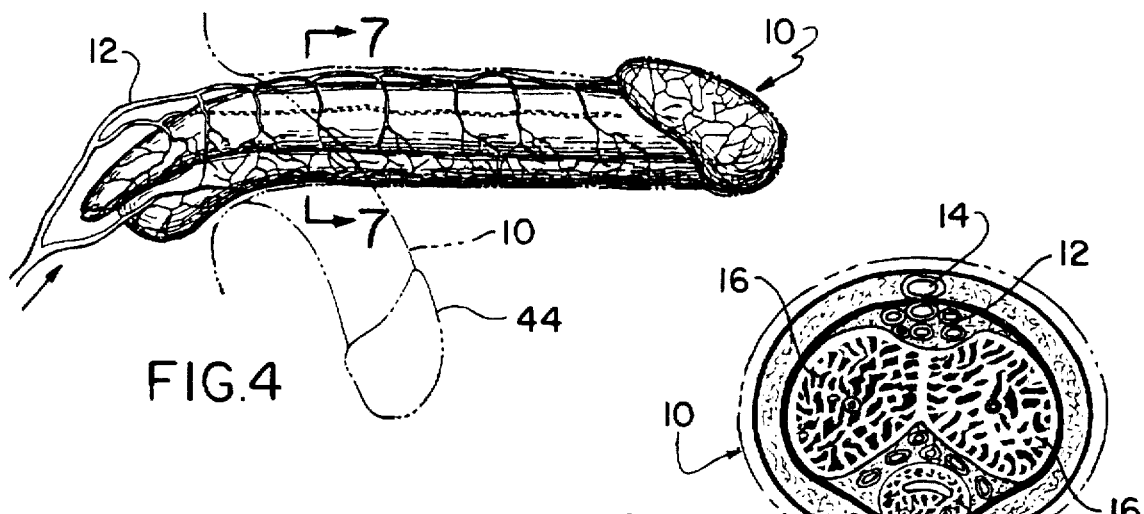
FIG.4  FIG.7
FIG.5
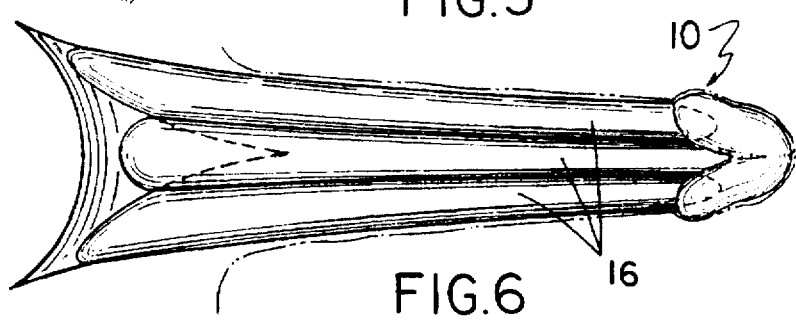
FIG.6

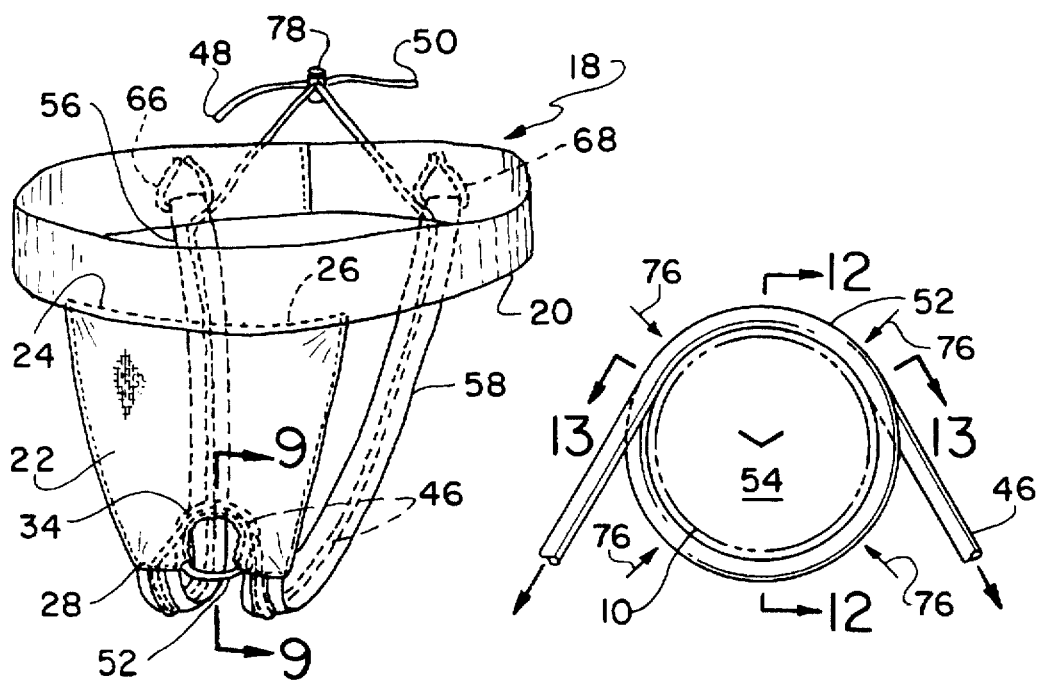
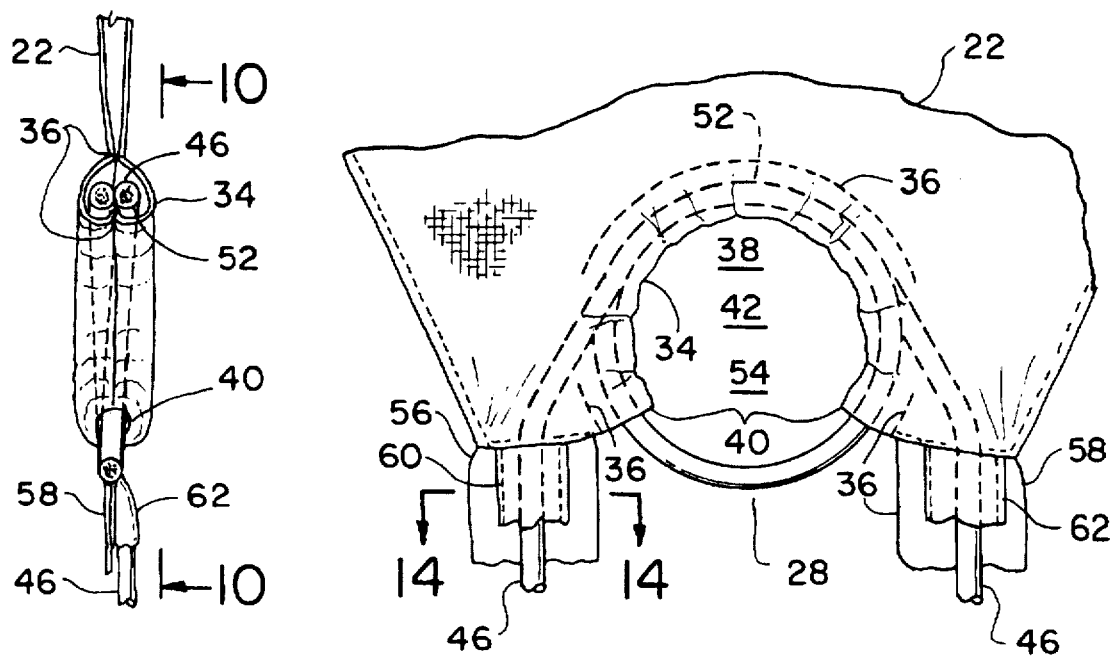

DEVICE FOR OBVIATING ERECTILE DYSFUNCTIONING

The present invention relates generally to improvements for obviating male impotence due to so-called venous leakage, the improvements more particularly taking into consideration and being accommodating to the individual main artery system of the penis of the user, all as will be better understood as the description proceeds.

EXAMPLES OF THE PRIOR ART

It is known from medical literature that the delicate balance of blood flow into and out of the penis controlled by "valves" within and muscles surrounding arteries and veins, determines whether a patient is able to achieve an erection of only a short duration, or none at all.

To prevent uncontrolled outgoing or exiting flow, known in medical parlance as venous leakage, prior patents propose devices which squeeze closed the network of veins of the artery system and, in this way, restrict the exiting blood in an attempt to correct the venous leakage.

These prior patents are exemplified by U.S. Pat. No. 4,539,980 issued to Chaney for "Male Organ Conditioner" on Sep. 10, 1985 and U.S. Pat. No. Des. 343,246 issued to Gaylor et al. for "Male Erection Sustainer" on Jan. 11, 1994, to mention but a few.

In the operating mode of exiting flow-restricting penis-encircling rings or the like, the extent of pressure applied to squeeze closed the artery system is dictated by size and construction material, and from a specific pressure so dictated by size and construction material. There is little or no deviation or range of pressures. With all known flow-resisting or constricting rings, it frequently occurs that the specific extent of applied pressure is insufficient to obviate venous leakage or, on the other extreme, is excessively high so as to prevent blood engorgement of the penis in the first instance.

Broadly, it is an object of the present invention to provide a blood flow-restricting device overcoming the foregoing and other shortcomings of the prior art.

More particularly, it is an object to provide a pressure-applying device to counter venous leakage having an operating mode of making available a range of pressures so that a user can select a pressure from the range, prior use of the device, as might be determined from trial and error that is most effective for his artery system, all to the end of maintaining an erectile penis condition.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a front elevational view of the within inventive device in use;

FIG. 2 is similar to FIG. 1, but illustrating the device in a side elevational perspective;

FIG. 3 is likewise a view similar to FIG. 1, but illustrating the device in a rear elevational perspective;

FIG. 4 is a side elevational view of a penis in its erectile condition illustrating the main artery system thereof;

FIGS. 5 and 6 are respectively plan and bottom views of the penis of FIG. 4 showing additional details of the main artery system thereof;

FIG. 7 is a cross sectional view taken along line 7—7 of FIG. 4;

FIG. 8 is a perspective view of the within inventive device;

FIG. 9 is a cross sectional view taken along Line 9—9 of FIG. 8;

FIG. 10 is a partial front elevational view taken along line 10—10 of FIG. 9;

FIG. 11 is a schematic view similar to FIG. 10 illustrating details of the operating mode of the inventive device;

Figure 12:
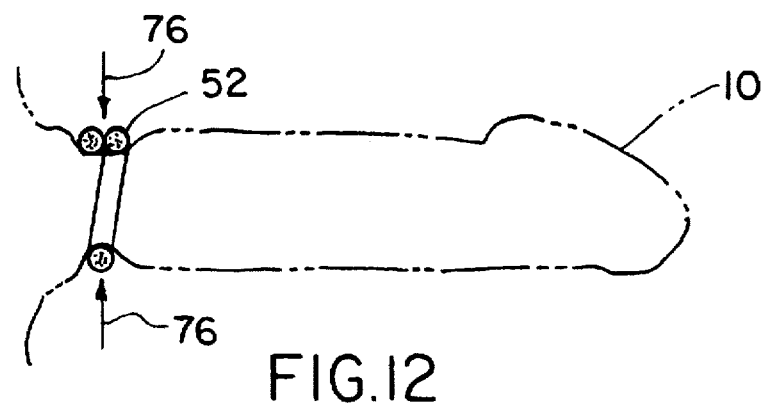
FIG. 12 is a schematic view similar to FIG. 4 but in outline perspective only to better illustrate the inventive device.
Figure 13:
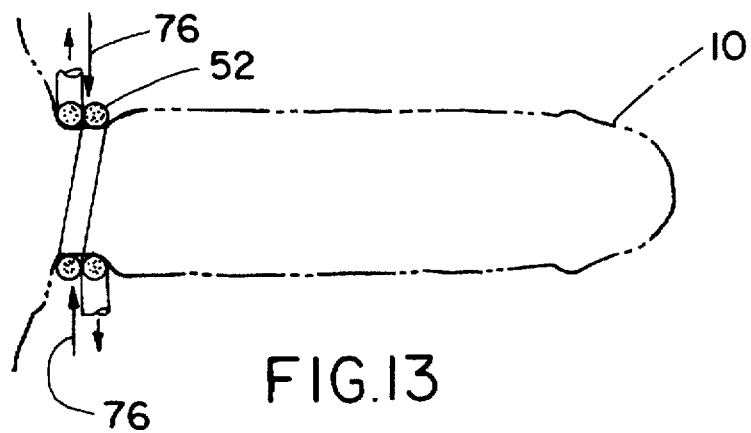
FIG. 13 is a schematic view similar to FIG. 5 and also in outline perspective.
Figure 14:
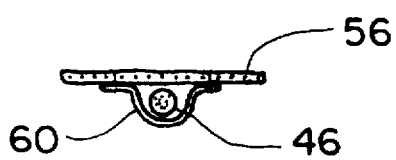
FIG. 14 is a detail sectional view taken along line 14—14 of FIG. 10.
Figure 15:
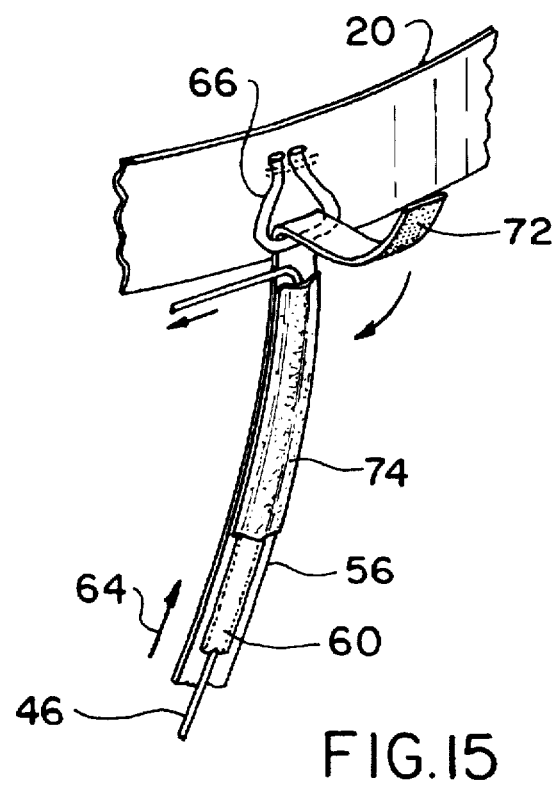
FIG. 15 is a partial perspective view of additional details of the construction of the within device.

Although the inventive device and the anatomy of the penis necessary for understanding the construction and operating mode of the within inventive device will be described in greater detail subsequently, it is helpful to note general aspects of FIGS. 4, 5, 6 and 7. In FIG. 4, penis 10 is shown in a flaccid condition, as noted by the triple dot reference line 44, and in full line as an erection which is the known condition preliminary to ejaculation, involving a complex interplay of brain, nerves, glands, muscles and blood vessels that combine as a reflex action initiated by physical and mental sexual stimulation. Most significant to the achieving of the erection are changes within the main artery system 12 which allow for an increase of blood to enter the three cylinders 16 of penis 10 (See FIGS. 6 and 7) through its many branches. For the duration of the erection there is a delicate balance of blood flow into and out of the penis 10 controlled by valves within and muscles surrounding arteries 12 and veins 14, resulting in the necessary differential blood pressure to maintain the erection.

In the case of pure venous impotence, the patient is found to have a difficulty in his ability to restrict the outflow of blood from the penis, which is classified as "venous leakage". Depending on the degree of disability, the patient is able to achieve an erection of short duration, or none at all.

The within inventive device, generally designated 18, includes a waist-encircling elastic belt 20 having an inverted, two ply isosceles triangular fabric panel 22 attached by stitching 24 adjacent its geometrical base 26 to extend in depending relation from the belt 20 so as to position its geometrical apex 28 in covering relation, as best illustrated in FIG. 1, over the crotch area 30 of a user 32. A sleeve 34 in stitched attachment, as at 36, to the panel apex 28 is disposed in an inverted U-shape configuration as noted at 38 and has edges 40 bounding a correspondingly inverted U-shape opening 42. Disposed in threaded relation through the sleeve 34 is a length potion of an elastic cord 46 having opposite ends 48 and 50 and which, between these ends, is formed into a helical coil 52 bounding a central opening 54 through which the user's penis 10 is projected preparatory to use of the device 18.

Completing the construction of the device 18 are two elastic straps 56 and 58 which each have sleeves 60 and 62 through which the cord ends 48 and 50 are threaded until extending from the ends of the sleeves 60 and 62 thus positioning the cord ends 48 and 50 in an out-of-way location rearwardly of the user 32 as best understood from FIG. 3

In grasping the combination strap 56, 58 and cooperating sleeve and elastic cord combination 60, 62 and 46, and urging these grasped components in a rearwardly pulling movement 64, (see FIG. 2) the straps 56 and 58 stretch so that their free ends can be looped through belt-attached loops 66 and 68 and held in a closed loop configuration 70 by cooperating connecting patches 72 and 74 to secure the device 18 in place on the user, and simultaneously the cord 46 is stretched producing an urgency in the elastic construction material which tightens the helical coil 52 about the base of the penis 10. The result of the tightening of the helical coil 52 is the application of a tourniquet-applied pressure 76 which constricts exiting blood flow from the penis 10 and, in practice, has been found to effectively significantly diminish so-called venous leakage.

In practicing the use of the device 18 the user 32 acquires an understanding of the extent of tourniquet pressure 76 that is needed to serve the purposes intended. When the appropriate pressure 76 is achieved, it is desirable to maintain this pressure which is conveniently done by using a friction clip 78 applied adjacent the cord ends 48 and 50, as best understood from FIG. 3.

Underlying the present invention is the recognition that a penis erection is a complex reflex action initiated by physical and mental sexual stimulation causing in the main artery system of the penis an increase of blood to enter the penis and, for the duration of the erection there is a delicate balance of blood flow into and out of the penis, controlled by "valves" within and muscles surrounding arteries and veins, providing the necessary differential blood pressure to maintain the erection, and thus to provide this "delicate" balance requires the ability to apply a range of flow-restricting pressure 76, a selected one pressure from the range being found to be, by trial and error, most effective for the individual main artery system 12 involved. This is in contrast to prior art constraint rings which apply a specified pressure in accordance with size and construction material and cannot significantly deviate from the specified pressure which if too low does not prevent venous leakage and if too high does not allow blood flow into the penis to provide an erectile condition in the first instance.

Optionally the cord-exposed lower portion of the helical coil 52 can be threaded through an additional sleeve (not shown) extending across the bottom of the inverted U-shape opening 42 to contribute to the comfort of the user.

While the apparatus for practicing the within inventive method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A device for obviating venous leakage of a type contributing to loss of an erecticle condition in a human's penis, said device comprising a belt adapted to be encircled about a user's waist, an inverted isosceles triangular panel having a base and sides attached adjacent said base in depending relation from said belt so as to be adapted to cover a user's crotch, a sleeve disposed in an inverted U-shape configuration having edges bounding a correspondingly inverted U-shape opening located in an apex of said isosceles triangular panel, a length portion of an elastic cord with opposite ends and between said ends in an assumed helical coil configuration operatively disposed in said sleeve, and a pair of straps connected in spanning relation from said inverted U-shape configuration to said waist-encircling belt, whereby urging said elastic cord opposite ends in pulling movement simultaneously secures said device in place on a user and applies a tourniquet pressure with a closing of said helical coil upon a penis disposed through said apex central opening so as to maintain an erectile condition in said penis with minimal venous leakage.

* * * * *